United States Patent [19]

Silberzahn

[11] 4,409,188

[45] Oct. 11, 1983

[54] CONTAINER STERILIZATION

[76] Inventor: Helmut Silberzahn, Hauptstrasse 72, Mosbach, Baden, Fed. Rep. of Germany, D-6950

[21] Appl. No.: 298,625

[22] Filed: Sep. 2, 1981

[30] Foreign Application Priority Data

Sep. 3, 1980 [DE] Fed. Rep. of Germany ....... 3033043

[51] Int. Cl.[3] ................................................ A61L 2/00

[52] U.S. Cl. .................................... 422/303; 210/760; 134/104; 422/24; 422/28

[58] Field of Search ............................. 422/24, 26–28, 422/268, 297, 300–306, 293; 210/627, 760; 134/104, 152, 100, 102

[56] References Cited

U.S. PATENT DOCUMENTS

| | | | |
|---|---|---|---|
| 3,302,655 | 2/1967 | Sasaki et al. | 134/152 |
| 3,946,750 | 3/1976 | Fischer et al. | 134/104 |
| 3,949,772 | 4/1976 | Hartmann | 134/104 |
| 4,280,520 | 7/1981 | Fraula et al. | 134/104 |

FOREIGN PATENT DOCUMENTS

| | | | |
|---|---|---|---|
| 689820 | 6/1964 | Canada | 422/28 |
| 2450765 | 4/1976 | Fed. Rep. of Germany | 422/28 |
| 2843387 | 4/1980 | Fed. Rep. of Germany | 422/302 |
| 2040150 | 8/1980 | United Kingdom | 422/24 |

OTHER PUBLICATIONS

Ozone Bids for Tertiary Treatment-Environmental Science and Technology, No. 11, vol. 4, pp. 893, 894.

*Primary Examiner*—Bernard Nozick

*Attorney, Agent, or Firm*—Schwartz, Jeffery, Schwaab, Mack, Blumenthal & Koch

[57] ABSTRACT

A device for the sterilization of containers is described. The device comprising a housing with inlet and outlet openings and being fluid tight apart from said openings, an axially rotatable immersion wheel located within the housing and having a plurality of individual cells, each for receiving one of a number of containers to be sterilized, which cells are disposed on the circumference of said wheel and at an oblique angle enabling containers therein to drop therefrom when the cell is approximately level with said axis of the immersing wheel, said wheel being rotatable stepwise, each step corresponding to the angle of the arc between adjacent cells, the housing enclosing a sterilizing agent immersion bath the level of which is below said axis, wherein said sterilizing agent immersion bath is in an immersion trough and contains ozone in an ozone and water mixture which may be added to the immersion bath in the immersion trough, and wherein variable gaseous ozone enrichment is maintained with the aid of at least one spray nozzle delivering an ozone and fresh-water solution and/or mixture.

7 Claims, 3 Drawing Figures

CONTAINER STERILIZATION

DESCRIPTION

Figures 1, 1A:
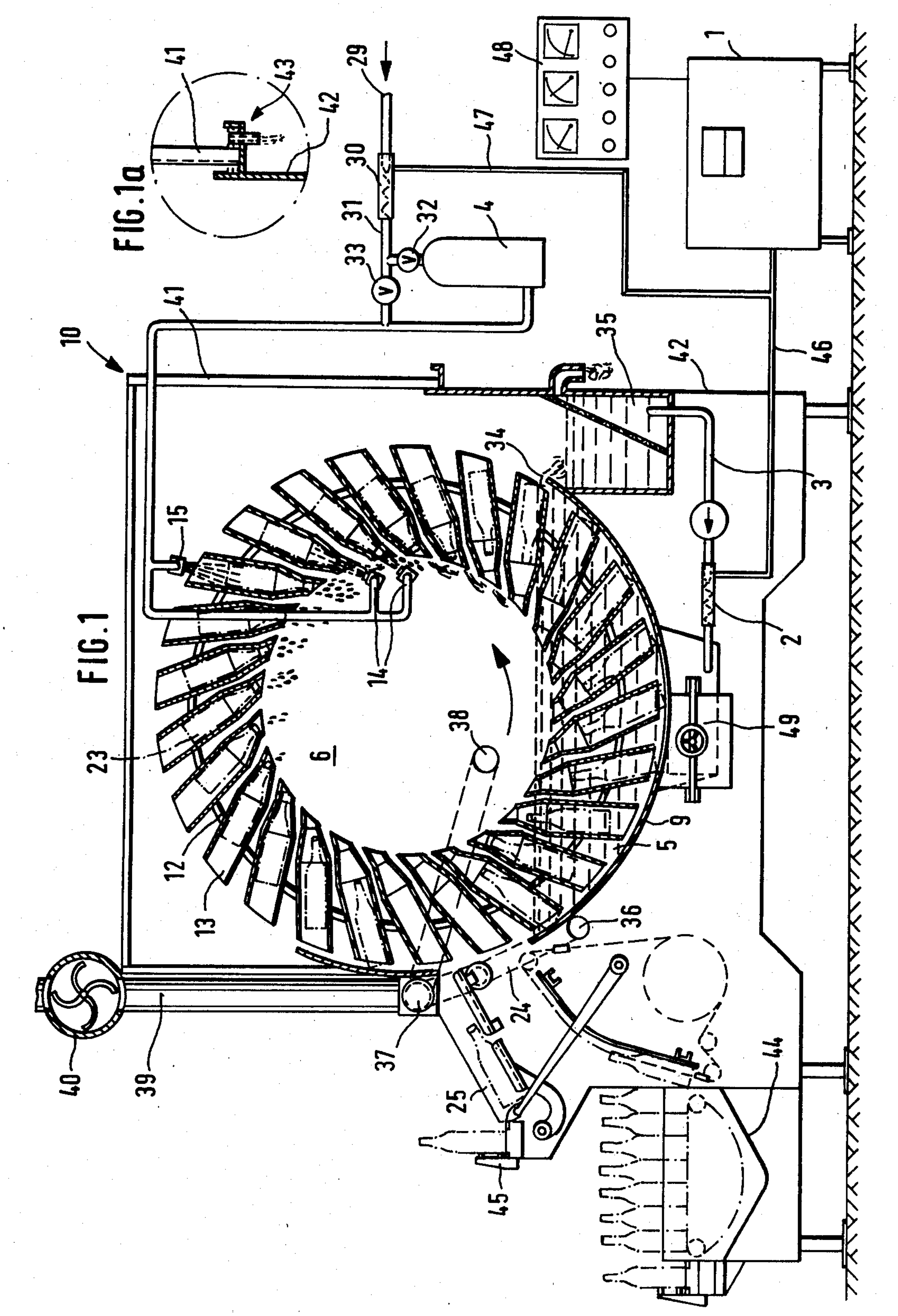

The invention relates to a device for the sterilisation of containers. In particular the invention concerns the cold sterilisation of containers (such as ampoules or bottles), the device comprising a housing with inlet and outlet openings and being fluid tight apart from said openings, an axially rotatable immersion wheel located within the housing and having a plurality of individual cells, each for receiving one of a number of containers to be sterilised, which cells are disposed on the circumference of said wheel and at an oblique angle enabling containers therein to drop therefrom when the cell is approximately level with said axis of the immersing wheel, said wheel being rotatable stepwise, each step corresponding to the angle of the arc between adjacent cells, the housing enclosing a sterilising agent immersion bath the level of which is below said axis.

Cleaning devices of this kind for bottles are disclosed in DT PS No. 1 206 751. In this and similar devices, the bottles are sterilised using sulphurous acid which is produced, for example, by introducing $SO_2$ gas into water. The $SO_2$ gas is supplied from a gas bottle and passed into water so that the desired sulphurous acid forms. Maintaining a lower than ambient pressure in the housing of the steriliser ensures that, as far as possible, no $SO_2$ gas escapes.

The use of sulphur in the form of sulphurous acid as an oxidation agent is particularly suitable when sterilising wine bottles as any residual trace of sulphur has no excessively disadvantageous effects on the bottled wine. However, the use of sulphur as a basic substance for the oxidation agent for sterilising bottles has other considerable drawbacks which have to be overcome at relatively high cost. For example, because of the ever tighter environmental legislation, the spent sulphur compounds cannot simply be added to the waste water. The sulphur compounds cannot be discharged until the sulphur has been washed out with the aid of soda lye, and thus suitable holding tanks must be provided. Apart from this any sodium hydroxide formed still needs to be neutralised, necessitating the addition of appropriate amounts of peroxide. To be able to discharge one kilogram of sulphurous acid, for example, three kilograms of other chemicals have to be added, which not only adds to the amount of undesirable substances carried in the waste water, but also makes the cost higher.

Moreover, when sulphur compounds are used as oxidation agents, there is also the danger of attack if any of the safety devices fail when, for example, residues of sulphurous acid are left unnoticed in the wine bottles being sterilised and these are then filled with wine.

The waste gases also constitute a hazard to the environment and, here again, considerable sums have to be invested in plant to prevent or keep to an extremely low level any escape of $SO_2$ gases to the atmosphere.

The use of ozone is already known for disinfecting drinking water and extensive experience has been gained regarding its behaviour. In addition, tests have been undertaken with a view to using ozone in the gas phase for sterilisation. One such process is disclosed in German Pat. No. 598 606 by way of example. However, attempts of this kind have been reduced to practical application so far as ozone is extremely unstable in its gas phase. Since ozonisation can only be carried out successfully if intensive contact is ensured with the items being sterilised in the presence of water, it must be remembered that, for the task at hand, degradation of the ozone must not occur before the mixture has reached the point of treatment. To achieve this, it is known for the formation of the mixture of the ozonised air with the water to be delayed until just before the point of application and for the mixture to be conveyed to the point of application so rapidly that premature degradation is no longer possible. However, it has been found that the production of the mixture of ozonised air and water immediately before the point of application is not straightforward but entails considerable expense.

Another difficulty arises when sterilising containers since these have to be sterilised internally and externally, and spraying is not enough in most cases.

The invention is based on the knowledge that ozone, a very powerful oxidation agent, is especially suitable for sterilising containers, particularly when mixed and/or dissolved in water.

Therefore, an underlying aim of the invention is to provide a device with the aid of which it is possible to achieve adequate sterilisation of containers by a continuous process using ozone as the sterilising agent, the device being designed in such a way that the articles being sterilised remain in satisfactory contact with the sterilising agent, internally and externally, for a sufficient time and, in addition, an adequate and practically constant ozone concentration is present at all times.

According to the invention there is provided a device for sterilising containers the device comprising a housing with inlet and outlet openings and being fluid tight apart from said openings, an axially rotatable immersion wheel located within the housing and having a plurality on individual cells, each for receiving one of a number of containers to be sterilised, which cells are disposed on the circumference of said wheel and at an oblique angle enabling containers therein to drop therefrom when the cell is approximately level with said axis of the immersing wheel, said wheel being rotatable stepwise, each step corresponding to the angle of the arc between adjacent cells, the housing enclosing a sterilising agent immersion bath the level of which is below said axis, wherein said sterilising agent immersion bath is in an immersion trough and contains ozone in an ozone and water mixture which may be added to the immersion bath in the immersion trough, and wherein variable gaseous ozone enrichment is maintained with the aid of at least one spray nozzle delivering an ozone and fresh-water solution and/or mixture.

The ozone gas produced by an ozone generator may be fed to injectors with the aid of which it is, firstly, mixed with fresh water and, secondly, mixed with used water coming from the immersion bath via a collector, the ozone and fresh-water mixture being passed through spraying nozzles to the inside of the containers and spraying nozzles to the outside of the containers and falling freely into the immersion bath, and the ozone and used-water mixture being added to the immersion bath in the region of the deepest part of the immersion trough.

It is advantageous to dispose an enrichment container controllable by means of control valves, in a bypass to the ozone and fresh-water line.

In one development of the invention, an overflow is disposed at the end of the immersion bath in the direction of rotation of the immersion wheel, said overflow running into a collector which has means for removing contaminating substances and carrying off surplus ozone and water mixture.

Gas intake openings (connected to the outside air by means of a gas discharge line with a fan) may be disposed above and/or below the container inlet opening and the container outlet opening and approximately in the centre of the housing to keep the pressure therein at a certain level below that outside. The housing may have detachable top and bottom parts enabling its disassembly for cleaning and/or maintenance, and the wall of the top part may be hermetically connected to the bottom part by means of a water labyrinth seal to ensure adequate gastightness.

Radiation sources emitting Ultra Violet light may be provided to increase and/or maintain the ozone concentration in the gaseous or dissolved liquid phase.

Figure 2:
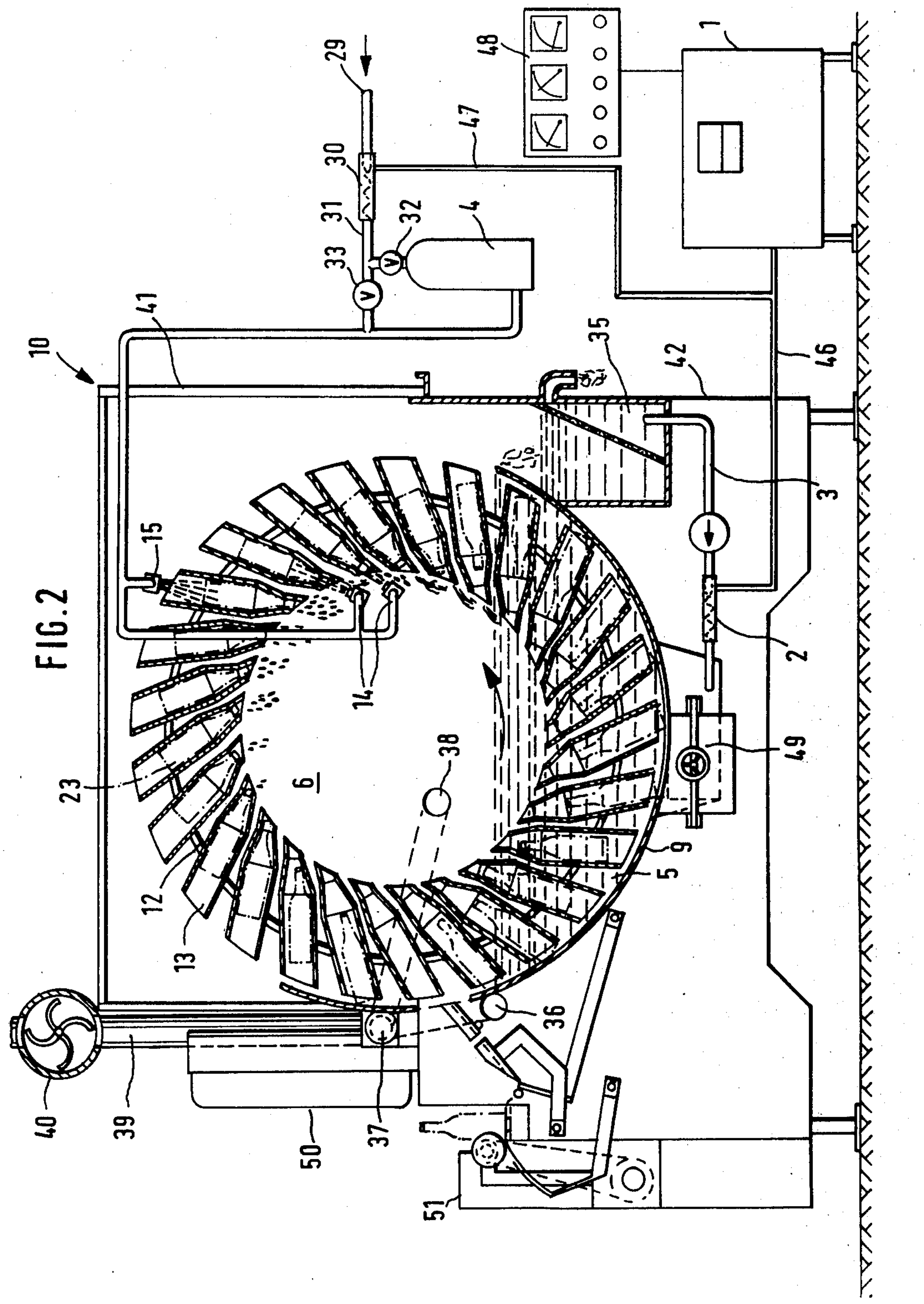

Embodiments of the invention will now be described with reference to the accompanying drawings in which:

FIGS. 1 & 1*a*, illustrates in cross-section a sterilising device embodying the invention, and FIG. 2, illustrates in cross-section the embodiment of FIG. 1 having modified bottle loading and discharge arrangements.

The device for the cold sterilisation of bottles shown in FIG. 1 has a housing 10 formed of a top part 41 and a bottom part 42. The bottom part 42 accommodates a trough 9 holding the immersion bath 5 and a collector 35 which directly adjoins the immersion trough 9.

Inside the housing 10 there is a immersion or drum wheel 12 which is movable with the aid of a drive (not shown) and on the circumference of which individual cells 13 are fixed to take bottles 23 to be sterilised. The individual cells 13 are essentially tubular in form, have solid walls, and are mounted on the drum wheel 12 at an oblique angle as shown to enable bottles placed therein to drop out on their own as will be described below. A bottle insertion device 44 is provided to introduce bottles 23 into cells 13 via a loading opening 24. A table conveyor 45 is used to receive the sterilised bottles via a bottle discharge opening 25 and to carry them away.

An ozone generator 1 produces ozone gas which is fed to an injector 2 and an injector 30 via ozone-resistant lines 46 and 47 respectively. Polytetrafluorethylene (which is also distributed under the brand name Teflon) may be used for the ozone-resistant delivery line material although other suitable materials may be used. Fresh water passes to injector 30 along a line 29 and is mixed with the ozone streaming from the line 47. An enrichment container 4 lies in a bypass to the ozone and fresh water line 31; this enrichment container may be filled with ozone and fresh water by operating valves 32 and 33 so that the ozone generator 1 may work continuously even if the demand for ozone and fresh water fluctuates.

The ozone and fresh-water line 31 supplies first and second nozzles 14 and 15, the first nozzles 14 spraying the interior bottles in the individual cells 13 while the second nozzle 15 ensures sterilisation of the bottles 23 from outside.

The ozone and fresh-water mixture passes through chamber 6 in housing 10 and falls into the immersion bath 5, and via an overflow 34 into a collector 35 from which a line 3 leads to the injector nozzle 2 which, as noted above, is supplied with ozone gas via line 46 and thus ensures renewed enrichment of the used water originating from the collector 35 with ozone.

The ozone and used-water mixture from injector 2 is fed into the immersion bath 5 in the region of the deepest part of the trough 9 so that the ozone gas bubbles which still have not dissolved in the water stream through the immersion bath, during which a further part of the gas goes into solution. Some two thirds of the total ozone gas production is fed to the immersion bath 5 via the injector 2 whilst one third of the ozone gases produced passes via the injector 30 and the nozzles 14 and 15 into the gas chamber 6 and the immersion bath 5. In addition to providing adequate buffering, the enrichment container 4 in the bypass to the ozone and fresh-water line 31 also promotes the dissolution of the ozone in the water.

Gas intake openings 36, 37 and 38 (connected to the air outside via a gas discharge line 39 and a fan 40) are disposed above and below the container insertion opening 24, the container discharge opening 25 and approximately in the centre of the housing 10 respectively, so that a lower than ambient pressure can be maintained in the gas chamber 6 above the immersion bath 5. The gas intake openings 36 and 37 also ensure that no ozone escapes into the working area.

A water labyrinth seal 43 (see FIG. 1*a*) is provided between the detachable top part 41 of the housing 10 and the bottom part 42 so that the chamber 6 is adequately gas-tight.

To carry out bottle sterilisation, the bottles are fed to the sterilising device via an intermittently operating feed conveyor acting in conjunction with the mechanism of the bottle insertion device 44 and pushed into a bottle cell 13. The cells with the bottles 23 inside them move through the immersion bath 5 step by step, fill with water in which ozone has been dissolved and the, as they are lifted clear of the bath, empty themselves. The bottles emerging from the immersion bath 5 pass through the spray zones of the nozzles 14 and 15, the nozzles 14 ensuring the bottles are sprayed internally and the nozzle 15 ensuring they are sterilised externally. The spraying zone of the nozzles 14 and 15 is immediately followed by a lengthy draining zone in the upper gas chamber 6 of the sterilising device which is filled with air containing ozone. On reaching the container discharge opening 25, the bottle slides onto the table conveyor 45, is stood upright and then passes to the bottling device not shown. During this, the bottle remains full of air containing ozone to guard against re-infection.

The ozone concentration in the ozone and water mixture of the immersion bath 5 and in the gas chamber 6 above the immersion bath 5 is brought about by regulating the ozone generator 1 with the aid, for example, of continuous pH monitoring or measurement of redox potential. These values are measured at the appropriate points in the immersion bath and the gas chamber by sensors (not shown in detail) and indicated to the operator by measuring equipment 48.

Since the ozone generator 1 is supplied with high voltage, it is expedient to erect this unit with its water cooling outside the wet environment of the bottling cellar. Transporting the ozone gas produced along the ozone resistant lines 46 and 47 to the injectors 2 and 30 located adjacent the sterilising device does not pose any technical problems.

The ozone achieves its maximum effect in water which is free of organic substances, and a temperature range of from 25° to 30° centigrade has proved to be particularly favourable. Inevitably, when processing used bottles fed to the sterilising device from the washing machine or treating new glassware, harmful substances as indicated previously are introduced into the immersion bath 5. Therefore, it is important to destroy these harmful substances as rapidly as possible, to remove them and prevent any accumulation in the bath in any circumstances. To carry off these harmful substances as quickly as possible, the overflow 34 is located at the end of the immersion bath 5 in the direction of rotational movement of the drum wheel 12, running straight into the collector 35 which has means for removing contaminating substances and carrying off surplus ozone and water mixture. The harmful substances are driven towards the overflow by the movement of the immersing wheel 12 and the bubbles of ozone gas introduced into the immersion bath 5 from below and thus pass into the collector 35. A broad overflow is provided at a suitable place on the collector 35 to wash out any labels, fibres, scraps of paper, dust or the like. The water in the collector 35 still contains some ozone as well so that it is scarcely contaminated and can be regarded as sterile. So, if this water is not required, it can be discharged directly without polluting the environment.

Under the ring of cells in the machine, at the deepest point in the immersion bath 5, there is a so-called fragment shaft 49 which extends over the full width and in which any glass fragments in the immersion bath collect and can be easily removed from the bath.

FIG. 1*a* is an enlarged view of the water labyrinth seal between the top part 41 of the housing 10 and the bottom part 42 thereof. For this the inner wall 42 is raised so that a vacuum can be maintained in the gas chamber 6 without the sealing water overflowing on the inside.

FIG. 2 shows a sterilising device constructed in the same way but with a different bottle loading and discharge arrangement. Here the bottles are fed to the sterilising device by means of a pressure feed 51 and leave the device through the same opening, but in a discharge device 50 disposed above it. A gas extraction line is provided, running over the entire width of the machine so that, here again, no ozone gases escape to the outside.

The ozone gases discharged via the gas discharge line 39 and the fan 40 degrade relatively quickly in oxygen so that no harmful effects on the environment occur.

The continuous influx of fresh water through the fresh water line 29 to the spraying zones and thus to the immersion bath 5 ensures ample, continuous, automatic cooling so no special cooling devices are needed in order to keep within the required temperature range between 25° and 30° centigrade.

The ozone concentration in the ozone/water mixture may be increased by the provision of suitably placed Ultra-Violet light sources, for example in the volume 6 of housing 10 above bath 5.

I claim:

1. An apparatus for sterilizing containers comprising:

a fluid-tight housing having a container inlet and a container outlet;

a plurality of container immersion cells axially mounted for rotation within said housing and at an oblique angle;

an immersion bath within said housing containing a fluid sterilizing agent comprising ozone and water;

a collector adjoining said bath within said housing for receiving excess fluid from said immersion bath, and means for variable enrichment of the gaseous ozone in said immersion bath, said means comprising at least one spray nozzle for spraying a mixture of ozone and fresh water into the area of said container immersion cells and at least one inlet to said immersion bath for supplying a mixture of ozone and said fluid from said collector.

2. The apparatus of claim 1 further comprising means for removing contaminants from said fluid in said collector.

3. The apparatus of claim 1 further comprising a gas discharge line in said housing above said immersion bath and means connected to said gas discharge line for reducing the pressure in said housing.

4. The apparatus of claim 1, wherein the top and bottom of said housing are removable.

5. The apparatus of claim 1, wherein said container immersion cells are tubular in shape and comprise solid walls.

6. The apparatus of claim 1 wherein said means for variable enrichment of ozone further comprising an ozone generator for supplying ozone to a fresh water source and ozone to said fluid from said collector.

7. The apparatus of claim 6, wherein said inlet to said immersion bath is at the lowest area of said bath.

* * * * *